United States Patent
Lucke et al.

(10) Patent No.: US 10,178,966 B2
(45) Date of Patent: Jan. 15, 2019

(54) DETECTION DEVICE FOR THE IN VIVO AND/OR IN VITRO ENRICHMENT OF SAMPLE MATERIAL

(71) Applicant: GILUPI GmbH, Potsdam OT Golm (DE)

(72) Inventors: Klaus Lucke, Werder (DE); Robert Niestroj, Berlin (DE); Andreas Bollmann, Berlin (DE)

(73) Assignee: GILUPI GMBH (DE)

( * ) Notice: Subject to any disclaimer, the term of this patent is extended or adjusted under 35 U.S.C. 154(b) by 484 days.

(21) Appl. No.: 14/290,180

(22) Filed: May 29, 2014

(65) Prior Publication Data

US 2014/0357967 A1    Dec. 4, 2014

(30) Foreign Application Priority Data

May 31, 2013   (DE) .......................... 10 2013 210 204

(51) Int. Cl.
*A61B 5/145* (2006.01)
*A61B 10/00* (2006.01)
(Continued)

(52) U.S. Cl.
CPC ...... *A61B 5/14503* (2013.01); *A61B 10/0045* (2013.01); *A61B 10/02* (2013.01); *G01N 33/54366* (2013.01); *A61B 2010/0216* (2013.01)

(58) Field of Classification Search
CPC . A61B 5/14503; A61B 10/02; A61B 10/0045; G01N 33/54366
See application file for complete search history.

(56) References Cited

U.S. PATENT DOCUMENTS 5,814,295 A     9/1998  Martin, Jr. et al.
6,396,995 B1 *  5/2002  Stuelpnagel ......... G01N 21/253
                                                385/115
(Continued)

FOREIGN PATENT DOCUMENTS

CN      1103431 A       6/1995
CN    101612035 A      12/2009
(Continued)

OTHER PUBLICATIONS

Flores et al., "Improving the yield of circulating tumour cells facilitates molecular characterisation and recognition of discordant HER2 amplification in breast cancer", British Journal of Cancer, 2010, pp. 1495-1502, vol. 102.
(Continued)

*Primary Examiner* — Melanie Brown
(74) *Attorney, Agent, or Firm* — The Webb Law Firm (57) ABSTRACT

The invention relates to a detection device for the in vivo and/or in vitro enrichment of sample material, comprising a functional surface charged with detection receptors. To ensure the diagnosis of different diseases using a detection device of the type mentioned at the outset with less efforts and an improved precision of the diagnosis, it is provided according to the invention that the detection device comprises at least one guide element and at least two functional elements disposed at the guide element, wherein a functional surface charged with detection receptors is formed at each of them, the functional elements being designed for being detachable from each other and/or individually detachable from the guide element. Furthermore, the invention provides a use of and a method for the application of said detection device.

14 Claims, 3 Drawing Sheets

(51) Int. Cl.
  *G01N 33/543* (2006.01)
  *A61B 10/02* (2006.01)

(56) References Cited

U.S. PATENT DOCUMENTS

| | | |
|---|---|---|
| 2008/0058676 A1 | 3/2008 | Yong |
| 2008/0241262 A1* | 10/2008 | Lee .................... A61K 9/0009 424/490 |
| 2011/0027913 A1* | 2/2011 | Bau .................... G01N 27/308 436/518 |
| 2011/0213270 A1 | 9/2011 | Pison |
| 2012/0237944 A1 | 9/2012 | Lücke et al. |
| 2012/0302916 A1 | 11/2012 | Pison et al. |
| 2013/0197334 A1 | 8/2013 | Weber et al. |

FOREIGN PATENT DOCUMENTS

| | | |
|---|---|---|
| WO | 2010025719 A1 | 3/2010 |
| WO | 2010145824 A1 | 12/2010 |
| WO | 2011047671 A1 | 4/2011 |
| WO | 2011113584 A1 | 9/2011 |

OTHER PUBLICATIONS

Saucedo-Zeni et al., "A novel method for the in vino isolation of circulating tumor cells from peripheral blood of cancer patients using a functionalized and structured medical wire", International Journal of Oncology, 2012, pp. 1241-1250, vol. 41.

* cited by examiner

DETECTION DEVICE FOR THE IN VIVO AND/OR IN VITRO ENRICHMENT OF SAMPLE MATERIAL

CROSS-REFERENCE TO RELATED APPLICATIONS

This application claims priority to German Patent Application No. 102 013 210 204.6 filed May 31, 2013, the disclosure of which is hereby incorporated in its entirety by reference.

The invention relates to a detection device for the in vivo and/or in vitro enrichment of sample material, comprising a functional surface charged with detection receptors.

While many cell types, molecules, tumor markers and biomarkers are present in body fluids, due to their low concentration, they often cannot be extracted by conventional enrichment processes in a sufficiently efficient manner to be subsequently used in established diagnostic methods of clinical chemistry, pathology or cytology.

For example, the enrichment of special cells, in particular circulating tumor cells, from a blood sample outside the body of a patient (in vitro) by means of commercially available paramagnetic nanoparticles and/or by density gradient centrifugation is possible, but only to a very restricted amount and involving the disadvantage of the nanoparticles binding to or in the cell and thereby possibly damaging them or aggravating diagnostics. One of these commercial methods is reflected in a test in which e.g. circulating tumor cells from a blood volume of 7.5 ml are enriched by means of paramagnetic nanoparticles to then be able to give statements on the course of disease.

The limiting factor of this method is the obtained sample volume which is much higher when a detection device for enriching sample material within the body of a patient (in vivo), e. g. a functionalized catheter, is employed. Vessel catheters for the application of medical interventions often have a cylindrical design. The advantage of this shape is its relatively low frictional resistance. However, with this shape, there is a risk in that the blood stream is constricted in relatively small blood vessels leading to the development of a thrombosis.

From the prior art in WO 2010/145824 A1, a detection device for the in vivo and/or in vitro enrichment of sample material is furthermore known, in case of which a functional surface charged with detection receptors comprises a three-dimensional structure with opposed functional sections forming spaces that can be interspersed with a sample liquid, thus reducing the risk of thromboses. According to WO 2010/145824 A1, the individual functional sections of the functional surface may be charged with chemically identical or chemically different detection receptors. If different detection receptors are provided, such a detection device may be employed, for example, for the diagnosis of different diseases.

The object underlying the invention is to provide a detection device of the type mentioned in the beginning by means of which the diagnosis of different diseases may be effected with less efforts and an improved precision of the diagnosis.

To achieve the object underlying the invention, a detection device for the in vivo and/or in vitro enrichment of sample material is provided, comprising at least one guide element for guiding at least one functional element, and at least two functional elements disposed at the guide element at each of which a functional surface charged with detection receptors is formed, the functional elements being designed for being detachable from each other and/or individually detachable from the guide element.

By the design of the functional elements which allows them to be detached from each other and/or by the arrangement of the functional elements in such a way that they may be individually detached from the guide element, these may be independently subjected to different methods of diagnosis. The diagnostics of different diseases may be thereby carried out more purposefully, thus involving less efforts.

The functional surface of a functional element may be charged with chemically identical or chemically different detection receptors. Thus, different ligands may also be enriched at a functional surface as required in one application. In a preferred manner, the functional surface of a functional element, however, is charged with detection receptors or a combination of detection receptors which differ from the detection receptors or the combination of detection receptors on the functional surface of the respective other functional element.

In the sense of this invention, all structures, in particular receptors or ligands, which are suited for capturing target molecules and target cells, are referred to as detection receptors. Furthermore, all target molecules and target cells that may dock to the detection receptors are referred to as ligands to simplify matters. The term sample liquid means a sample present in a liquid form.

Below, the term proximal is to refer to a direction, an end or an end section associated with a potential operator of the detection device. In contrast, the term distal is to refer to a direction, an end or an end section associated with a potential patient or a sample material to be examined.

Preferred further developments of the invention are the subject matter of the subclaims.

In an advantageous embodiment of the invention, the guide element preferably meets at least one of the following requirements:

The guide element is designed as a wire at least in sections.

The guide element is designed for being resilient at least in sections.

The guide element is designed as flexible medical guide wire at least in sections.

The guide element is designed as thread at least in sections.

The guide element is designed as flexible plastic thread at least in sections.

The guide element is designed as catheter at least in sections.

The guide element comprises a receiving section for receiving at least one functional element.

The guide element comprises a distal end and a proximal end, a receiving section for receiving at least one functional element being embodied between said distal and said proximal ends.

The guide element is designed like a screw at least in sections.

The guide element comprises an external thread at its outer periphery at least in sections.

The guide element comprises a distal end and a proximal end, wherein the distal end can be inserted into a blood vessel.

The guide element comprises a distal and a proximal end, the distal end being thickened.

The guide element comprises a distal end and a proximal end, the proximal end being connected to a stabilization element.

The guide element is screwed into an internal thread of the stabilization element.

The guide element is made of a metallic and/or a non-metallic material.

The guide element comprises a functional surface charged with detection receptors at its distal section.

According to a further advantageous embodiment of the invention, the guide element is connected with a stabilization element for stabilizing the at least one guide element which preferably meets at least one of the following requirements:

The stabilization element is designed for stabilizing the guide element at least in sections.

The stabilization element is made of plastics or metal.

The stabilization element is connected with a proximal end or a proximal end section of the guide element.

The stabilization element is detachably connected to the guide element.

The stabilization element is connected to the guide element by a positive, non-positive and/or by a material bond.

The stabilization element is glued or welded to the guide element.

The stabilization element has a cylindrical design at least in sections.

The stabilization element is designed as a sleeve at least in sections.

The stabilization element has an internal thread at least in sections.

The stabilization element is at least in sections pushed-on, put-on or screwed to a proximal section of the guide element.

The stabilization element is at least in sections pushed-on, put-on or screwed to a distal section of the guide element.

The stabilization element guides the guide element at least in sections.

The stabilization element guides the guide element in a movable manner.

The stabilization element is designed as covering device for at least one functional element.

The stabilization element comprises a reception in which the at least two functional elements are arranged.

The stabilization element may be inserted into a blood vessel.

The stabilization element comprises a reception in which the at least two functional elements are arranged so that they may be guided out.

The stabilization element comprises a distal and a proximal ends, wherein a thread, in particular a Luer-Lock thread, is embodied at the distal end for connecting retention cannulas.

The stabilization element comprises a push-pull device by means of which the at least two functional elements may be guided out of the sleeve and into it again.

The stabilization element comprises at least one section whose outer diameter corresponds or essentially corresponds to the outer diameter of the distal section of the guide element.

The stabilization element is fabricated with the guide element in one manufacturing process.

The stabilization element has a rounded end to protect from injuries.

The stabilization element is designed for stabilizing the joint between at least one of the functional elements and the guide element.

According to yet another advantageous embodiment of the invention, a covering device is furthermore provided which meets at least one of the following requirements:

The covering device is designed for covering at least one of the functional elements.

The covering device is part of the stabilization element.

The covering device is designed as component discrete from the stabilization element.

The covering device is designed for stabilizing the guide element at least in sections.

The covering device is made of plastics or metal.

The covering device has a cylindrical design at least in sections.

The covering device comprises a longitudinal bore for receiving at least one functional element.

The covering device is designed as a sleeve at least in sections.

The covering device is at least in sections pushed-on, put-on or screwed to a proximal section of the guide element.

The covering device may be inserted into a blood vessel.

The covering device comprises a reception in which the at least two functional elements are arranged so that they may be guided out.

The covering device is arranged movably along a longitudinal orientation relative to the functional elements and/or relative to the stabilization element.

The covering device comprises a distal and a proximal ends, wherein a thread, in particular a Luer-Lock thread, is embodied at the distal end for connecting retention cannulas.

The covering device comprises homopolymers, copolymers, biopolymers, chemically modified polymers, and/or synthetic polymers.

The covering device has a rounded end to protect from injuries.

The covering device is designed for covering the joint between at least one of the functional elements and the guide element.

According to another advantageous embodiment of the invention, at least one of the functional elements meets at least one of the following requirements:

The functional element is at least partially made of metal, preferably high-grade steel, medical high-grade steel, or titanium; of glass, preferably glass fiber; of plastics, preferably foamed plastic, a polymer, preferably polyethylene, polypropylene, polyurethane, polytetrafluoroethylene, a plastic based on organic polymers, or a combination of said materials.

The functional element is designed as flexible thread which preferably has a lower thickness and/or higher flexibility than the guide element.

The functional element is fixed to the distal end of the guide element, in particular to a cross-sectional surface of the distal end.

The functional element is fixed to the outer periphery of the guide element, wherein the length of the functional element is preferably longer than the distance of the joint at the outer periphery of the guide element from the distal end of the guide element.

The functional element is connected with at least one further functional element at its distal end, preferably with at least two further functional elements, preferably by a material connection.

The functional element is designed as a wire, in particular as a flexible wire, which preferably has a lower thickness and/or a higher flexibility than the guide element.

- The functional element is fixed to the distal end of the guide element, in particular to a cross-sectional surface of the distal end, in particular by a material bond, in particular welded to the cross-sectional surface of the distal end.
- The functional element is connected at its distal end with at least one further functional element, preferably with at least two further functional elements, in particular by a material bond, in particular welded.
- The functional element may be nondestructively detached from the at least one other functional element and/or nondestructively removed from the guide element.
- The functional element may be cut or torn off the guide element.
- The functional element is formed by an annular segment.
- The functional element has a spherical or bone shape.
- The functional element comprises an internal thread at its inner periphery.
- The functional element encloses at least one section of the guide element.
- The functional element is pushed-on, put-on or screwed to the guide element.
- The functional element is disposed at the guide element between a distal end and a proximal end thereof.
- The functional element comprises detection receptors which differ from the detection receptors of the respective other functional element.
- The functional element comprises a combination of detection receptors which differs from the combination of detection receptors of the respective other functional element.
- The functional element comprises at least one section having an outer diameter which corresponds or essentially corresponds to the outer diameter of the distal section of the guide element.
- The functional element comprises at least one section having an outer diameter which is greater or smaller than the distal section of the guide element, in particular 0.01 mm to 0.1 mm smaller than the distal section of the guide element.
- The functional element is designed as a stent, catheter or catheter section.
- The functional element is designed as a mandrain.
- The functional element is designed with elevations, indentations and/or branches.
- The functional element at least partially comprises a spiral, screw-shaped, worm-shaped, undulated, helical, filamentous, brush-like, comb-like, net-like, porous, spongy or similar structure.
- The functional element comprises a coating of metal, preferably of a metal of the $10^{th}$ or $11^{th}$ group of the periodic system of elements, preferably of nickel, copper, palladium, silver, platinum and/or gold.

According to a further embodiment of the invention, the functional surface of at least one functional element meets at least one of the following requirements:

- The functional surface comprises a three-dimensional structure with opposed functional sections which form at least one space that may be interspersed with a sample liquid, the space being preferably designed at least in sections like a channel, wherein preferably several spaces preferably form a branched network of channels.
- The functional surface is structured three-dimensionally on a macroscopic and/or microscopic scale.
- The functional surface is designed with elevations, indentations, and/or branches.
- The functional surface at least partially comprises a spiral, screw-shaped, worm-shaped, undulated, helical, filamentous, brush-like, comb-like, net-like, porous, spongy or similar structure.

The functional sections are considered as being opposed if they include an angle of less than 180 degrees, so they can "see" each other. Thereby, the detection device has a greater functional surface compared to a detection device with a plane or cylindrical functional surface. Furthermore, the sample liquid may be ideally directed over the functional surface in the spaces and enriched at the detection receptors. Moreover, the ligands docking to the detection receptors may be better retained in the spaces and thus be better protected from abrasion. Preferably, the functional surface may also store a certain volume of sample liquid.

It may prove helpful for the functional surface of at least one functional element to be structured three-dimensionally on a macroscopic and/or microscopic scale. By a functional surface that is three-dimensionally structured on a macroscopic or visible scale, which is determined, for example, by the visible geometry of the detection device, the sample liquid may be advantageously directed over the functional surface. By a functional surface that is three-dimensionally structured on a microscopic scale, the flow velocity in the region of the boundary layer may be reduced. The spaces are preferably dimensioned at least such that specific ligands may dock to the detection receptors. Preferably, the spaces are dimensioned such that approximately the number of specific ligands that corresponds to the number of detection receptors at the opposed functional sections may be received and arranged. Thereby, the functional surface is ideally utilized. Furthermore, the ligands may be even better protected from abrasion.

In an advantageous embodiment of the invention, the space is designed like a channel at least in sections, wherein several spaces preferably form a branched network of channels. The channel may extend across the total length of the functional surface. Thereby, sample liquid may be ideally directed to the detection receptors. By the design of the size of the spaces, a flow rate and a flow direction of the sample liquid may be influenced. Preferably, the channel extends in the longitudinal direction of the detection device at least in sections, so that the channel only has a minimal influence on a natural flow direction of the sample liquid.

It may be advantageous for the functional surface of at least one functional element to be designed with elevations, indentations, and/or branches, and/or to comprise at least partially a spiral, screw-shaped, worm-shaped, undulated, helical, filamentous, brush-like, comb-like, net-like, porous, spongy or similar structure. Such shapes have large surfaces and are well suited for being employed in the detection device according to the invention. Spiral, screw-shaped, worm-shaped, undulated, helical structures normally have a low frictional resistance. Thereby, the flow of sample liquid, for example blood in a blood vessel, is not largely affected, even if parts of the functional surface are lying against the vessel walls. Filamentous, brush-like, comb-like, net-like, porous and spongy structures decelerate the natural flow of the sample liquid and are perfectly suited as liquid storage whereby the enrichment of the ligands at the detection receptors is additionally promoted.

It may prove advantageous for the detection receptors to comprise antibodies, antibody fragments, amino acid structures, nucleic acid structures, inorganic materials, and/or synthetic structures with a specific affinity to cell surfaces, preferably monoclonal antibodies of murine origin, chimeric antibodies or humanized antibodies, preferably HLA-G and/or EpCAM antibodies.

It may also be practical for the functional surface of at least one functional element to comprise saturated groups of atomics and covalently bound ligands and receptors to prevent undesired interactions with blood ingredients and the docking of nonspecific cells and molecules.

The handling of the detection device may furthermore be facilitated by the guide element, the at least two functional elements, the stabilization element, and/or the covering device being joined into a stiletto.

However, it may also be practical for the guide element, the stabilization element, and/or the covering device to comprise a mark for application control. Thereby, the detection device may be better controlled when it is being used.

In another advantageous embodiment of the invention, at least one of the functional elements comprises a biocompatible polymer which preferably meets at least one of the following requirements:

The biocompatible polymer is designed as coherent polymer layer. Thereby, the complete surface of the functional element may be covered or shielded by the polymer layer. The thickness of the polymer layer is preferably within a range of 0.1 to 10 µm, preferably within a range of 0.5 to 5 µm, particularly preferred within a range of 1 to 2 µm.

The biocompatible polymer comprises a three-dimensional, preferably filamentous and/or porous structure. This structure forms many spaces which are essentially filled by the ligands docking to the detection receptors, so that the ligands are even better protected from abrasion. The biocompatible polymer may be three-dimensionally structured on a macroscopic and/or a microscopic scale.

The biocompatible polymer comprises a three-dimensional, preferably filamentous and/or porous surface. The surface of the biocompatible polymer may be three-dimensionally structured on a macroscopic and/or microscopic scale.

The biocompatible polymer comprises a carbonaceous, branched molecular structure. This molecular structure is perfectly suited for the docking of the detection receptors and the enrichment of ligands to the detection receptors. Said molecular structure moreover forms a filamentous functional surface in the sense of the invention which is three-dimensionally structured on a microscopic scale. The branched molecular structures comprise numerous spaces which are formed by opposed functional sections charged with detection receptors in the form of polymer molecules. Said spaces may be interspersed with a sample liquid and form a liquid storage, whereby the enrichment of the ligands at the detection receptors becomes particularly supported. In the region of the boundary layer at a surface populated with this molecular structure, the flow of sample liquid is considerably decelerated. This additionally supports the enrichment of ligands.

The biocompatible polymer is preferably actively connected to the functional element via functional groups, preferably by a chemical bond, particularly preferred by a covalent bond.

The biocompatible polymer comprises functional groups, preferably carboxylic groups, the functional groups preferably comprising an uncompensated molecular charge by chemical activation, wherein the functional groups are preferably adjusted to the detection receptors.

The biocompatible polymer has hydrophilic properties and preferably is a hydrogel.

The biocompatible polymer comprises chemically and/or enzymatically fissible groups which facilitates the detachment of ligands. The chemically and/or enzymatically fissible groups are preferably the functional groups to which the detection receptors are bound.

The biocompatible polymer comprises saturated groups of atoms and covalently bound detection receptors to prevent undesired interactions with blood ingredients and the docking of nonspecific cells and molecules.

The biocompatible polymer is arranged in a cavity of the functional element. Thereby, a cavity of the functional element may be used for the enrichment of ligands. There, the ligands are optimally protected from abrasion.

The biocompatible polymer is cross-linked.

The biocompatible polymer comprises or forms the functional surface. The functional surface is preferably located at the surface of the biocompatible polymer. The biocompatible polymer may be directly charged with the detection receptors.

In yet another advantageous embodiment of the invention, the functional surface is coated with a protective layer, the protective layer preferably meeting at least one of the following requirements:

The protective layer is soluble in liquids, in particular in body liquids, preferably in blood. Thereby, the functional surface may be automatically exposed as soon as the protective layer comes into contact with the sample liquid.

The protective layer is biocompatible. Thereby, defense responses of the body are largely prevented in the in vivo application of the detection device.

The protective layer is organically crystalline and comprises at least one of the following components: alginates, preferably highly purified alginates, polyethylene glycols, cyclic and non-cyclic oligosaccharides, polysaccharides, antioxidative amino acids, proteins, or vitamins. Such components are biocompatible and readily soluble.

It may be useful for the detection receptors to be actively connected to the functional surface, preferably to the carrier and/or the biocompatible polymer, preferably via linkers or organic functional groups, preferably by a chemical bond, preferably by a covalent bond. Thereby, a nonspecific adsorption at the functional surface may be largely prevented.

A further independent aspect of the invention relates to a detection device, preferably according to at least one of the preceding claims, manufactured by:

providing a detection device having at least one guide element for guiding at least one functional element, and having at least two functional elements, chemically activating the functional elements by a chemical, preferably covalent bond of the detection receptors directly or via a biocompatible polymer to functional groups of the functional elements, preferably to organic functional groups of the functional elements, preferably via sulfurous and/or nitrogenous compounds.

The detection device may comprise each of the above-mentioned features.

Yet a further independent aspect of the invention relates to the use of a detection device according to one of the preceding embodiments for enriching samples, preferably from the blood vessel system, from efferent glandular ducts of the pancreas, of lacrimal glands, parotid glands, from efferent glandular ducts of mucous glands, mixed glands, cutaneous and sebaceous glands, mammary glands, spinal canals, cerebral ventricle systems, peridural spaces, gall bladders and their efferent anatomic structures, efferent urinary tracts or lymphatic systems, body cavities of the abdomen, the rib cage, the uterus, the urogenital apparatus, a joint or the gastrointestinal tract.

When using a detection device according to one of the preceding embodiments, the detection device may be introduced into a vessel system via a vessel access independent of the intended purpose.

It will be understood that a detection device according to one of the preceding embodiments may be used for endoscopic applications.

In particular, one aspect of the invention relates to the use of a detection device according to one of the preceding embodiments for the invasive enrichment of sample material, for the elimination of drugs, for the elimination of radioactive tracers, for the elimination of magnetic beads, for the extraction of tumor markers or biomarkers, and/or for the elimination of toxins, or for the enrichment of cells, comprising embryonal trophoblasts, disseminated tumor cells, in particular of haematogenously metastasizing tumors. By this, the mentioned advantages may be achieved.

Furthermore, a detection device according to one of the preceding embodiments may be advantageously used for the invasive enrichment of sample material, for the elimination of drugs, for the elimination of radioactive tracers, for the elimination of magnetic beads, for the extraction of tumor markers or biomarkers, and/or for the elimination of toxins, or for the enrichment of cells, comprising embryonal trophoblasts, disseminated tumor cells, in particular of haematogenously metastasizing tumors.

However, the invention also relates to the use of a detection device according to one of the preceding embodiments for enriching samples for diagnoses, in particular prenatal diagnosis, cancer diagnosis and therapy follow-up, and for the diagnosis of a disease selected from the group consisting of genetic diseases, proliferative diseases, inflammatory diseases, autoimmune diseases, infectious diseases, hormonal diseases, diseases of the blood and blood-building organs, diseases of the digestive tract, the liver, the gall, the pancreas, diseases of the urogenital tract and the kidney, diseases of the heart, pathological changes of the blood vessel system and the lymphatic system, diseases of the lung, diseases of the central or peripheral nervous system and the electric stimulus transport, and/or neurodegenerative diseases.

Here, the prenatal diagnosis may include the diagnosis of gene mutations, chromosome mutations, and chromosome aberrations from the group of a deletion, inversion, duplication, a translocation of ring chromosomes, a disorder of gene transcription, gene translation, mRNA stability, a splice variant, a disorder of the mRNA transport into the cytoplasma, protein biosynthesis, and/or an epigenetic factor.

In the present case, the cancer diagnosis may include primary diagnostics, diagnostics of tumor spread, and/or tumor grading. Furthermore, the therapy follow-up may include the monitoring of a tumor treatment, the monitoring of an autogenetic, syngenic, allogenic, xenogenic, or alloplastic transplantation, the monitoring of an inflammatory disease, the monitoring of an infectious disease, the monitoring of a hormonal disease, the monitoring of a psychiatric disease, and/or the monitoring of a neurodegenerative disease.

Genetic diseases for the diagnosis of which a detection device according to one of the preceding embodiments may be used may be selected from the group comprising autosomal recessive, autosomal dominant, gonosomal, mitochondrial, and/or extrachromosomal genetic diseases, and/or diseases attributed to a genetic disposition.

In contrast, proliferative diseases diagnosed using a detection device according to one of the preceding embodiments may be tumors, precanceroses, dysplasiae, neuroendocrine tumors, endometrioses, and/or metaplasiae.

Furthermore, however, the invention also includes the use of a detection device according to one of the preceding embodiments for enriching samples for the diagnosis of an autoimmune disease, said autoimmune disease being selected from the group comprising rheumatoid arthritis, inflammatory bowel disease, osteoarthritis, neuropathic aches, alopecia areata, psoriasis, psoriathritic arthritis, acute pancreatitis, allograft rejection, allergies, allergic inflammations of the lung, multiple sclerosis, Alzheimer disease, Crohn's disease, and/or systemic lupus erythematous.

Equally, a detection device according to one of the preceding embodiments for enriching samples may be used for the diagnosis of an infectious disease, the infectious disease being selected from the group comprising parasitic diseases, bacterial diseases, and/or viral diseases.

Hormonal diseases which may be diagnosed using a detection device according to one of the preceding embodiments may be selected from the group comprising a disease of glucose metabolism, lipometabolism, protein metabolism, sexual development and reproduction, water-salt balance, growth and/or cell formation.

Yet another independent aspect of the invention relates to a method for enriching sample material using a detection device according to at least one of the preceding embodiments, the method comprising the following steps:
  providing a detection device according to at least one of the preceding claims,
  introducing the detection device into a living organism,
  applying a sample liquid of the living organism to the functional surfaces of the at least two functional elements,
  enriching sample material, preferably cells, DNA, RNA, proteins, peptides, synthetic molecules, at the detection receptors,
  withdrawing the detection device from the living organism.

After the above-mentioned procedure steps, the functional elements may be advantageously detached from each other and/or be individually detached from the guide element and subsequently be independently provided for a respective suited diagnostic method.

The detection device may comprise each of the above-mentioned features.

Preferred further developments of the invention result from combinations of the subclaims or the partial features mentioned therein.

DETAILED DESCRIPTION OF THE PREFERRED EMBODIMENTS

The preferred embodiments of the invention will be described below with reference to the enclosed drawings.

First Embodiment

Figures 1, 2, 3, 4:
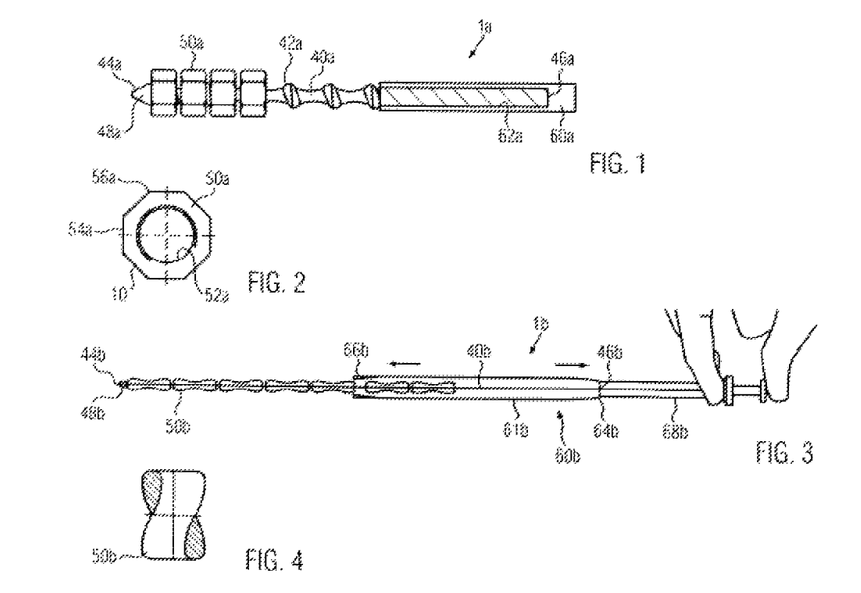
FIG. 1 is a schematic representation of a detection device of the invention according to a first embodiment.
FIG. 2 is a schematic cross-sectional representation of a functional element according to a first embodiment.
FIG. 3 is a schematic representation of a detection device of the invention according to a second embodiment.
FIG. 4 is a schematic representation of a functional element according to a second embodiment in a sectional longitudinal view.

FIG. 1 is a schematic representation of a detection catheter 1a according to a first embodiment. The detection device 1a of the invention according to the first embodiment comprises a flexible medical guide wire 40a which has a threaded structure, in particular an external thread 42a, at its outer periphery. The guide wire 40a furthermore comprises a distal end 44a and a proximal end 46a. A conical boundary 48a is formed at the distal end 44a of the guide wire 40a.

Furthermore, the detection device 1a comprises a stabilization element 60a which is arranged for stabilizing and fixing the guide wire 40a. The stabilization element may be designed as cylindrical sleeve 60a at the inner periphery of which an internal thread 62a is formed at least in sections. The guide wire 40a may be screwed into the cylindrical sleeve 60a via its distal end 46a.

The detection device 1a furthermore comprises at least two functional elements 50a which are screwed onto the guide wire 40a. Preferably, more than two functional elements 50a are screwed onto the guide wire 40a. The functional elements are prismatic or cylindrical ring segments 50a at the inner periphery of which an internal thread 52a is formed, as is shown in FIG. 2. The outer periphery 54a of a functional element 50a may be provided with eight surface sections and edges 56a defining the surface sections, so that the respective functional element 50a may be handled like a screw nut and be thereby easily screwed onto the guide wire 40a.

For screwing the functional elements 50a onto the guide wire 40a, the stabilization element 60a must be removed from the guide wire 40a. The functional elements 50a may be correspondingly screwed onto the guide wire from the proximal end 46a of the latter. The functional element 50a that was the first one to be screwed on will come to lie against the conical boundary 48a at the distal end 44a of the guide wire. Each further functional element 50a which is screwed onto the guide wire 40a may come to lie against the respective previously screwed-on functional element 50a. After the respective required number of functional elements 50a has been arranged, the guide wire may be screwed into the stabilization element embodied as cylindrical sleeve via its proximal end 46a.

To provide the individual functional elements 50a for subsequent diagnostic methods after the in vivo and/or in vitro enrichment of sample material by means of the detection device 1a, the guide wire 40a is first screwed out of the stabilization element 60a, so that the functional elements 50a may be then individually screwed off the guide wire 40a.

Each of the functional elements 50a has a functional surface 10 charged with detection receptors 12, wherein the functional surface 10 may be charged with one type of detection receptors 12 or with a combination of detection receptors 12. Here, it may be advantageous for the functional surface 10 of a functional element 50a to be charged with detection receptors 12 or a combination of detection receptors 12 which differ from the detection receptors 12 or the combination of detection receptors 12 of the at least one other functional element 50a. In this manner, the detection device 1a may be purposefully configured for the different intended uses or diagnoses with functional elements 50a comprising different detection receptors 12 or different combinations of detection receptors 12. By the functional elements 50a being arranged so that they may be detached from each other or be individually detached from the guide wire 40a, the different functional elements may be purposefully subjected to different diagnostic methods which follow the respective in vivo and/or in vitro enrichment of sample material.

Second Embodiment

FIG. 3 is a schematic representation of a detection catheter 1b according to a second embodiment. The detection device 1b of the invention according to the second embodiment is a biofunctionalized, medical detection catheter for the invasive (in vivo) enrichment of rare cells, biomolecules or drugs. Such a detection catheter or detector is also referred to as medical nano-catheter (MN-C).

The detection device 1b of the invention according to the second embodiment comprises a guide element 40b. The guide element 40b may be embodied as flexible medical guide wire, for example of a metallic material, or be embodied as plastic thread. The guide element 40b has a distal end 44b and a proximal end 46b. At the distal end 44b, an enlargement 48b is formed as boundary.

Furthermore, the detection device 1b comprises a stabilization element 60b which is arranged for stabilizing and fixing the guide element 40b. The stabilization element may comprise a sleeve 61b through which the guide element 40b is guided. The sleeve 61b may furthermore be connected to a push-pull device 68b via its proximal end 64b. The guide element 40b may be connected to the push-pull device 68b via the proximal end 46b to be thus moved by the push-pull device 68b relative to the sleeve 61b. The sleeve 61b furthermore has, at its distal end 66b, a Luer-Lock thread for connecting it to retention cannulas.

The detection device 1b furthermore comprises at least two functional elements 50b which are pushed or put onto the guide element 40b. Preferably, more than two functional elements 50b are pushed or put onto the guide element 40b. The functional elements may be ring segments 50b which may have, for example, a spherical or bone shape. In the longitudinal section shown in FIG. 3, the functional elements have a bone shape. In a state where the functional elements 50b are pushed or put on the guide element 40b, the latter is stabilized without flexibility being completely lost.

For pushing or putting the functional elements 50b onto the guide element 40b, the latter must be separated from the push-pull device 68b and located outside the sleeve 61b. The functional elements 50b may be correspondingly pushed or put onto the guide element 40b from the proximal end 46b thereof. The functional element 50b which was the first one to be pushed on will come to lie against the boundary 48b at the distal end 44b of the guide element 40b. Each further functional element 50b which is pushed onto the functional element 40b may come to lie against the previously pushed on functional element 50b. After the respective required number of functional elements 50b has been arranged, the guide element 40b may be pushed via its proximal end 46b into the sleeve 61b. The proximal end 46b of the guide element 40b may be guided out of the sleeve 61b through the proximal end 64b thereof to be connected to the push-pull device 68b. The latter may then be connected with the proximal end 64b of the sleeve 61b. The functional elements 50b may be stored within the sleeve 61b.

For the in vivo and/or in vitro enrichment of sample material by means of the detection device 1b, for example a retention cannula connected to the distal end 66b of the sleeve 61b is inserted into a human body. By means of the push-pull device 68b, now the guide element 40b including the functional elements 50b may be applied from the sleeve 61b into the respective body opening and subsequently be moved again into the sleeve 61b.

To make the individual functional elements 50b available for subsequent diagnostic methods, after the in vivo and/or in vitro enrichment of sample material by means of the detection device 1b, first the push-pull device 68b is detached from the sleeve 61b, then the guide element is removed from the push-pull device 68b and pulled out of the sleeve 61b. The functional elements 50b may subsequently be detached from the guide element 40b individually.

Each of the functional elements 50b has a functional surface 10 charged with detection receptors 12, reference being made to the above description of the first embodiment.

Third Embodiment

Figure 5:
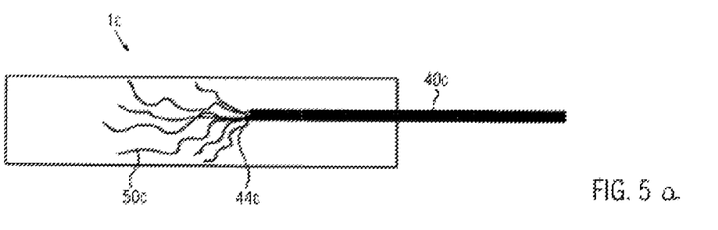
FIG. 5a is a schematic representation of a detection device of the invention according to a third embodiment.
FIG. 5b is a schematic representation of a detection device of the invention according to a fourth embodiment.

FIG. 5a is a schematic representation of a detection catheter 1c according to a third embodiment. The detection device 1c of the invention according to the third embodiment also is a biofunctionalized, medical detection catheter for the invasive (in vivo) enrichment of rare cells, biomolecules or drugs. As was already illustrated above, such a detection catheter or detector is also referred to as medical nano-catheter (MN-C).

The detection device 1c of the invention according to the third embodiment comprises a flexible medical guide wire 40c with a distal end 44c and a proximal end. The detection device 1c according to the third embodiment may furthermore be equipped with a stabilization element in the form of a sleeve (not represented here) and a pull-push device (not represented here). Insofar, reference is made to the second embodiment and the corresponding figures.

The detection device 1c furthermore comprises at least two functional elements 50c which are designed as threads. The threads 50c are, according to the third embodiment, firmly connected to the guide wire 40c at the free distal end 44c thereof. Preferably, the threads 50c have a lower thickness than the guide wire 40c. The thickness of the threads 50c should be in particular selected such that no thromboses are caused during their application. Simultaneously, the thickness of the threads should be selected such that these do not stick to each other but uniformly distribute in the blood flow.

The flexibility of the threads 50c may ensure, when a detection device 1c is employed, that the total vein cross-section is covered and moreover a freedom of motion in the longitudinal direction and across the longitudinal direction of the respective vein is given. The threads 50c thus form a tentacular structure when applied. Since the complete vein cross-section is covered thereby, a good enrichment of sample material from blood is ensured.

To make the individual functional elements designed as threads 50c available for subsequent diagnostic methods, after the in vivo and/or in vitro enrichment of sample material by means of the detection device 1c, the threads 50c may be individually cut or torn off the guide wire 40c.

Each of the functional elements 50c has a functional surface 10 charged with detection receptors 12, wherein reference being made to the above description of the first or second embodiment.

Fourth Embodiment

Figure 5B:
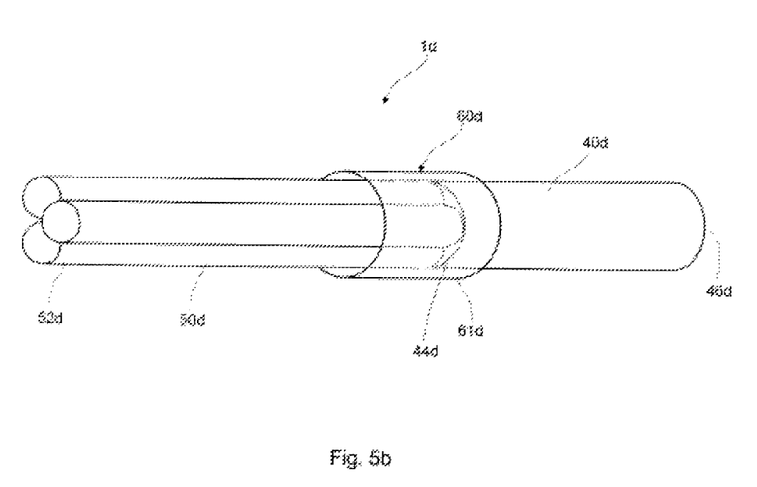

FIG. 5b is a schematic representation of a detection catheter 1d according to a fourth embodiment. The detection device 1c of the invention according to the second$_{[f1]}$ embodiment also is a biofunctionalized, medical detection catheter for the invasive (in vivo) enrichment of rare cells, biomolecules or drugs. As was already illustrated above, such a detection catheter or detector is also referred to as medical nano-catheter (MN-C).

The detection device 1d of the invention according to the fourth embodiment comprises a flexible medical guide wire 40d with a distal end 44d and a proximal end 46d. The detection device 1d according to the fourth embodiment may furthermore be equipped with a pull-push device (not represented here). Insofar, reference is made to the second embodiment and the corresponding figures.

The detection device 1d furthermore comprises at least two functional elements 50d, preferably more than two functional elements 50d, which are embodied as wires. The wires 50d are, according to the fourth embodiment, firmly connected, in particular welded, to the free distal end 44d of the guide wire 40d. The detection device 1d may be furthermore equipped with a stabilization element 60d in the form of a sleeve which preferably covers, in particular surrounds, the joint between the wires 50d and the distal end 44d of the guide wire 40d. Furthermore, the wires 50d are connected to each other, in particular welded to each other, at their distal ends 52d, so that the wires 50d altogether form a bundle of functional elements 50d.

Preferably, the wires 50d each have a lower thickness than the guide wire 40d. The thickness of the wires 50d should be in particular selected such that no thromboses are caused during their application. Simultaneously, the thickness of the wires 50d should be selected such that they may be easily guided through the guide wire 40d in a bundle.

To make the individual functional elements designed as wires 50d available for subsequent diagnostic methods, after the in vivo and/or in vitro enrichment of sample material by means of the detection device 1d, the wires 50d may be individually cut or torn off the guide wire 40d. Moreover, it is possible to release the connection present between the wires 50d at their ends 52d, which may be, for example, a welded joint, by tearing or cutting it to finally achieve a separation of the wires 50d.

Each of the functional elements 50d has a functional surface 10 charged with detection receptors 12, wherein reference being made to the above description of the first or second embodiment.

Functional Surface and Carrier of the Functional Surface

Figure 6:
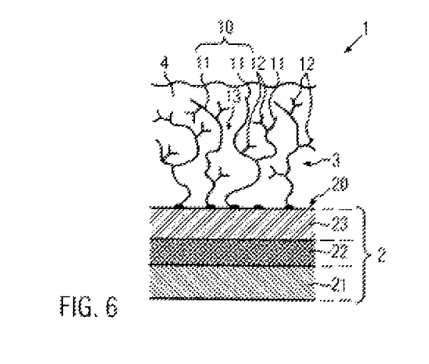
FIG. 6 shows an exemplary layer structure of a carrier.

According to the invention, the functional surface 10 may be embodied at a carrier 2. The carrier 2 may be part of a functional element 50a, 50b or 50c. An exemplary layer structure of a carrier 2 is shown in FIG. 6.

A substrate 21 of medical high-grade steel with a diameter of about 0.5 mm imparts its visible structure to the carrier 2. The substrate 21 may comprise one or several coatings 22, 23. Preferably, the substrate 21 is coated with a gold coating 22 having a thickness of 0.5 to 1.0 μm applied by galvanic methods, ceramic methods, cementation or by vapor-deposition. The substrate 21 may furthermore be coated with a biocompatible dye to reduce the autofluorescence of the basic material during microscopic evaluation.

The chemical activation of the carrier 2 is effected via an affinity reaction, in most cases by sulfurous or nitrogenous compounds, to which in turn specific detection receptors 12 may be bound directly or via polymer chains.

Preferably, a covalent secondary layer consisting of a functional biocompatible polymer 3 is applied to the carrier 2 via wet-chemical or physical methods. The layer thickness may be 1 to 2 μm. Thereby, the carrier 2 is chemically activated. By the surface finishing and chemical activation, specific antibodies, in particular monoclonal antibodies of murine origin, chimeric antibodies, humanized antibodies, or fragments of said antibodies or amino acid structures or nucleic acid structures or synthetic structures with a specific affinity to cell surfaces or molecules may be covalently bound as detection receptors 12.

It is just in a complex sample liquid such as blood that not only a permanent docking of the detection receptors 12 while preserving the biological function, but also an efficient suppression of nonspecific adsorption processes for the selective docking of the ligands is of utmost importance.

An intermediate layer 23 here has the task of ensuring an effective shielding of the surface of the substrate 21 and simultaneously providing the functional groups for the bond of the biocompatible polymer layer 3 in a sufficient density. The intermediate layer system accordingly forms a bonding agent between the gold coating 22 of the substrate 21 and the biocompatible polymer layer 3.

The biocompatible polymer 3 is preferably a hydrogel with carbonaceous, long branched macromolecules which have a high number of functional groups, e. g. carboxylic groups and/or polycarboxylates. The type of functional groups is based on the molecule properties of the specific detection receptors 12. The biocompatible hydrogel thereby ensures the permanent covalent bond of the detection receptors 12 while preserving the biological function and simultaneously prevents the detection receptors 12 from being affected in their detection function by nonspecific adsorption phenomena. Hydrogels are three-dimensionally cross-linked hydrophilic polymers which absorb liquids, such as water, but are not soluble therein themselves. The main ingredients of the hydrogel are polyacrylic acid (PAA) and polyethylene glycol (PEG). By a suited selection of the monomer units, the degree of cross-linking, and the density of cross-linking, property profiles may be tailored depending on the desired requirements or applications. An essential property is the biocompatibility, i. e. the compatibility of the hydrogel with the living tissue. By the branched polymer chains of the biocompatible polymer 3, however, the thrombogenic effect during the invasive application is also prevented. By chemical activation, the functional groups obtain an unbalanced molecule charge which permits to electrostatically attract dissolved detection receptors 12 from a solution and bind them covalently. The detection receptors 12 permanently immobilized at the polymer layer 3 serve the specific bonding of the ligands or target molecules and target cells via their surface antigens and thus permit the function of the detection device 1. Additionally, chemically or enzymatically fissible groups may be contained in this biocompatible polymer 3 to facilitate the quantitive extraction of bound target molecules or cells.

The branched molecular structures of the biocompatible polymer 3 form a functional surface 10 which is three-dimensionally structured on the microscopic scale with opposed functional sections 11 and spaces 13 that can be interspersed with sample liquid. While the surface of the carrier 2 three-dimensionally structured on the macroscopic or visible scale (FIG. 6) directs the sample liquid advantageously over the respective functional element 50a, 50b, 50c, the functional surface 10 of the biocompatible polymer 3 three-dimensionally structured on the microscopic scale (cf. FIG. 6) decelerates the stream of the sample liquid in the region of the boundary layer and abets the enrichment of the ligands at the detection receptors 12.

A biocompatible protective layer (tertiary layer or stabilization layer) 4 is applied over the biocompatible polymer 3 for preservation and for protecting it from the conditions of final sterilization, and as a radiation protection and for imparting durability to the product. Said protective layer 4 dries over the secondary layer and forms a dense network of crystalline structures and thus stabilizes and preserves the functional part 1a of the catheter 1. The protective layer 4 is not covalently bound. In the blood stream, the protective layer 4 dissolves and exposes the functional surface 10 of the catheter. As an alternative, the protective layer 4 may be washed with sterile water before the application.

The protective layer 4 may include highly purified alginates, polyethylene glycols, cyclic and non-cyclic oligosaccharides and polysaccharides, antioxidative amino acids, proteins and vitamins. The protective layer 4 preferably consists of a biocompatible highly viscous polysaccharide which serves as medium for added amino acids, proteins, vitamins and stabilizing polysaccharides. The high viscosity permits a rapid wettability of the surface. The applied protective layer 4 adheres to the secondary coating and prevents foreign substances from penetrating during its storage. The added amino acids, proteins and vitamins are present in higher concentrations, compared to the specific ligands, and thereby able to attract or hold off the probability of a damage to the target molecules by radical molecules or charge carriers and to restore chemical bonds destroyed by recombination processes.

The finished detection device 1a, 1b, 1c is packed in an almost sterile environment. Final sterilization is effected by means of gamma irradiation with a radiation dosage of 25 kGy. The detection device 1a, 1b, 1c is intended for a single application.

Application of a Detection Device According to the Invention

The detection device 1a, 1b, 1c, manufactured according to the invention with a refined functional surface 10 and with coupled detection receptors 12, is suited for the extraction of rare cells from blood circulation. This includes, for example, the following applications:

extraction of embryonic trophoblasts from the mammary blood circulation with e. g. specific antibody fragments (F(ab) fragments) and murine monoclonal antibodies (IgG) which can identify the cell surface protein HLA-G typical of trophoblasts.

extraction of disseminated tumor cells, in particular haematogenously metastasizing tumors e. g. with the humanized antibody anti-EpCAM which identifies the cellular surface protein EpCAM typical of many cancer cells.

A preferred application of the detection device 1a, 1b, 1c are prenatal and cancer diagnostics. The detection device 1a, 1b, 1c may be employed, for example, for isolating fetal cells or tumor cells circulating in the blood circulation of pregnant women or cancer patients. For the application, the detection device 1a, 1b, 1c is inserted into the vein via a suited, commercially available needle (Braunuele) system and applied into the venous blood circulation. The residence time in the vein may be about 30 min. After the detection device 1a, 1b, 1c has been removed from the bloodstream, the cells bound on the detection device 1a, 1b, 1c are further enriched by means of purposeful laboratory diagnostics and characterized moleculubiologically and cytologically.

It is the aim of the minimal-invasive method to be carried out to select fetal or tumor cells out of the blood. Due to the low cell concentration of the cells in the blood, a blood withdrawal of about 0.5 l would be necessary to obtain the desired number of target cells. This, however, is excluded from a medical view.

In prenatal diagnostics, a possible chromosome aberration (e. g. trisomy 21 (Down's syndrome)) is to be detected with the aid of the fetal cells contained in the mothers blood. Down's syndrome has been up to now only securely diagnosed prenatally by invasive methods which, however, involve a risk of abortion of 1%, chorionic villus biopsy between the $11^{th}$ and $14^{th}$ week of gestation, and amniocentesis as of the $15^{th}$ week of gestation. In contrast, the method according to the invention, which will be applicable as of the $9^{th}$ week of gestation, does not involve any risk for the fetus and may be employed in the first trimester screening. Thus, one can do without amniocenteses.

Fetal trophoblast cells from the placenta can be detected in the blood circulation of the mother as of the $6^{th}$ week of gestation. Only about 2 to 5 of these cells per ml of the mothers blood are present. These trophoblast cells have a membrane-bound HLA-G complex (antigen) which binds to certain antibodies. Preferably, a specific HLA-G antibody is employed as detection receptor 12 which only reacts with membrane-bound HLA-G (antigen) and thus is to capture only the desired fetal cells from the mother's blood.

Cancer tumor cells may be enriched with the EpCAM antibody (against the EpCAM antigen) which is humanized in its constant domains and is covalently bound to the hydrogel.

The invention claimed is:
1. A detection device for in vivo and/or in vitro enrichment of sample material, comprising at least one guide element for guiding at least one functional element and at least two functional elements disposed on at least a single guide element of the at least one guide element, each functional element having a functional surface independently charged with detection receptors, wherein the functional elements are individually attached to each other and/or the at least one guide element and are detachable from each other or the at least one guide element, wherein at least one of the at least one functional element is formed by an annular segment which is screwed to the at least one guide element, or wherein at least one of the at least one functional element is designed as flexible thread and/or flexible wire, which is fixed to the distal end of the at least one guide element by a material bond.

2. The detection device according to claim 1, in which:
   a. the at least one guide element is a wire, at least in sections;
   b. the at least one guide element is resilient, at least in sections;
   c. the at least one guide element is a flexible medical guide wire, at least in sections;
   d. the at least one guide element is threaded, at least in sections;
   e. the at least one guide element is a flexible plastic thread, at least in sections;
   f. the at least one guide element is designed as a catheter, at least in sections;
   g. the at least one guide element has a receiving section for receiving at least one functional element;
   h. the at least one guide element has between a distal end and a proximal end, a receiving section for receiving at least one functional element;
   i. the at least one guide element is helical, at least in sections;
   j. the at least one guide element has, at its outer periphery, an external thread, at least in sections;
   k. the at least one guide element is thickened at its distal end;
   l. the at least one guide element is made of a metallic and/or a non-metallic material; and/or
   m. the at least one guide element has a functional surface charged with detection receptors at a distal section.

3. The detection device of claim 1, in which the at least one guide element is connected to a stabilization element for stabilizing the at least one guide element.

4. The detection device of claim 3, in which:
   a. the stabilization element is made of a plastic or metal;
   b. the stabilization element is connected to a proximal end or a proximal end section of the at least one guide element;
   c. the stabilization element is detachably connected to the at least one guide element;
   d. the stabilization element is connected to the at least one guide element with a positive, non-positive or material bond;
   e. the stabilization element is glued or welded to the at least one guide element;
   f. the stabilization element has a cylindrical design, at least in sections;
   g. the stabilization element is designed as a sleeve, at least in sections;
   h. the stabilization element has an internal thread, at least in sections;
   i. the stabilization element is at least in sections pushed-on, put-on or screwed to a proximal section of the at least one guide element;
   j. the stabilization element is at least in sections pushed-on, put-on or screwed to a distal section of the at least one guide element;
   k. the stabilization element guides the at least one guide element, at least in sections;
   l. the stabilization element guides the at least one guide element in a movable manner;
   m. the stabilization element is designed as covering device for at least one functional element;
   n. the stabilization element has a reception in which the at least two functional elements are arranged;
   o. the stabilization element has a reception in which the at least two functional elements are arranged so that they can be guided out;
   p. the stabilization element has a distal end and a proximal end, with a threaded portion, at the distal end for connecting a retention cannula;
   q. the stabilization element has a push-pull device for guiding the at least two functional elements in and out of the sleeve;
   r. the stabilization element has at least one section whose outer diameter corresponds or essentially corresponds to an outer diameter of the distal section of the at least one guide element;

s. the stabilization element has a rounded end as protection against injuries; and/or
t. the stabilization element is designed for stabilizing the joint between at least one of the at least one functional element and the at least one guide element.

5. The detection device according to claim 1, further comprising a cover, in which:
   a. the cover is designed for covering at least one of the at least one functional element;
   b. the cover is part of a stabilization element connected to the at least one guide element for stabilizing the at least one guide element;
   c. the cover is designed as a component discrete from a stabilization element connected to the at least one guide element for stabilizing the at least one guide element;
   d. the cover is designed for stabilizing the at least one guide element, at least in sections;
   e. the cover is made of plastics or metal;
   f. the cover has a cylindrical design at least in sections;
   g. the cover has a longitudinal bore for receiving at least one functional element;
   h. the cover is designed as a sleeve, at least in sections;
   i. the cover is at least in sections pushed-on, put-on or screwed to a proximal section of the at least one guide element;
   j. the cover has a reception in which the at least two functional elements are arranged so that they can be guided out;
   k. the cover is movably arranged along a longitudinal orientation relative to the functional elements and/or relative to the stabilization element;
   l. the cover has a distal end and a proximal end, and comprising a thread at the distal end for connecting a retention cannulas;
   m. the cover comprises homopolymers, copolymers, biopolymers, chemically modified polymers, and/or synthetic polymers;
   n. the cover comprises a rounded end as protection against injuries; and/or
   o. the cover is designed for covering a joint between at least one of the at least one functional element and the at least one guide element.

6. The detection device according to claim 1, in which:
   a. at least one of the at least one functional element is at least partially made of metal, of glass, of plastics, a polymer, or a combination of said materials;
   b. at least one of the at least one functional element is designed as flexible thread which has a smaller thickness and/or a higher flexibility than the at least one guide element;
   c. at least one of the at least one functional element is fixed to the distal end of the at least one guide element;
   d. at least one of the at least one functional element is fixed to the outer periphery of the at least one guide element, the length of the functional element being longer than the distance of the joint at the outer periphery of the at least one guide element from the distal end of the at least one guide element;
   e. at least one of the at least one functional element is connected at its distal end with at least one further functional element by a material bond;
   f. at least one of the at least one functional element is designed as a flexible wire, which has a lower thickness and/or a higher flexibility than the at least one guide element;
   g. at least one of the at least one functional element is fixed to the distal end of the at least one guide element by a material bond;
   h. at least one of the at least one functional element is connected at its distal end to at least one further functional element by a material bond;
   i. at least one of the at least one functional element is nondestructively detached from the at least one other functional element and/or nondestructively detached from the at least one guide element;
   j. at least one of the at least one functional element is configured to be cut or torn off the at least one guide element;
   k. at least one of the at least one functional element is formed by an annular segment;
   l. at least one of the at least one functional element has a spherical or bone shape;
   m. at least one of the at least one functional element comprises an internal thread at its inner periphery;
   n. at least one of the at least one functional element encloses at least one section of the at least one guide element;
   o. at least one of the at least one functional element is pushed-on, put-on or screwed to the at least one guide element;
   p. at least one of the at least one functional element is arranged between a distal end and a proximal end of the at least one guide element at the latter;
   q. at least one of the at least one functional element comprises detection receptors which differ from the detection receptors of the respective other functional element;
   r. at least one of the at least one functional element comprises a combination of detection receptors which differs from the combination of detection receptors of the respective other functional element;
   s. at least one of the at least one functional element has at least one section of an outer diameter which corresponds or essentially corresponds to the outer diameter of the distal section of the at least one guide element;
   t. at least one of the at least one functional element comprises at least one section of an outer diameter which is larger or smaller than the distal section of the at least one guide element;
   u. at least one of the at least one functional element is designed as stent, catheter or catheter section;
   v. at least one of the at least one functional element is designed as a mandrain;
   w. at least one of the at least one functional element is designed with elevations, indentations, and/or branches;
   x. at least one of the at least one functional element at least partially comprises a spiral, screw-shaped, worm-shaped, undulated, helical, filamentous, brush-like, comb-like, net-like, porous, spongy or similar structure; and/or
   y. at least one of the at least one functional element comprises a coating of a metal of the 10th or 11th group of the periodic system of elements.

7. The detection device according to claim 1, in which:
   a. the functional surface of at least one functional element comprises a three-dimensional structure with opposed functional sections which form at least one space that may be interspersed with a sample liquid, the space being designed at least in sections like a channel, where several spaces form a branched network of channels;

b. the functional surface of at least one functional element is three-dimensionally structured on the macroscopic and/or microscopic scale;
c. the functional surface of at least one functional element is designed with elevations, indentations, and/or branches; and/or
d. the functional surface of at least one functional element at least partially comprises a spiral, screw-shaped, worm-shaped, undulated, helical, filamentous, brush-like, comb-like, net-like, porous, spongy or similar structure.

8. The detection device of claim 1, in which the detection receptors comprise antibodies, antibody fragments, amino acid structures, nucleic acid structures, inorganic materials and/or synthetic structures with a specific affinity to cellular surfaces.

9. The detection device of claim 1, in which at least one of the at least one functional element comprises a biocompatible polymer.

10. The detection device of claim 9, in which:
a. the biocompatible polymer is designed as a coherent polymer layer;
b. the biocompatible polymer has a three-dimensional structure;
c. the biocompatible polymer has a-filamentous and/or porous surface;
d. the biocompatible polymer has a carbonaceous, branched molecular structure;
e. the biocompatible polymer is actively connected to the functional element via functional groups by a chemical bond;
f. the biocompatible polymer comprises functional groups, wherein the functional groups comprise an uncompensated molecular charge by chemical activation, wherein the functional groups are adjusted to the detection receptors;
g. the biocompatible polymer comprises hydrophilic properties and is a hydrogel;
h. the biocompatible polymer comprises chemically and/or enzymatically fissible groups;
i. the biocompatible polymer comprises saturated groups of atoms and covalently bound ligands and receptors;
j. the biocompatible polymer is arranged in a cavity of the functional element;
k. the biocompatible polymer is cross-linked; and/or
l. the biocompatible polymer comprises and/or forms the functional surface.

11. The detection device of claim 1, in which the at least one functional surface is coated with a protective layer.

12. The detection device of claim 11, in which:
a. the protective layer is soluble in liquids;
b. the protective layer is biocompatible; and/or
c. the protective layer is organically crystalline and comprises at least one of the following components: alginates, polyethylene glycols, cyclic and non-cyclic oligosaccharides, polysaccharides, antioxidative amino acids, proteins, or vitamins.

13. A method for enriching sample material, comprising:
a. providing a detection device according to claim 1;
b. inserting said detection device into a living organism;
c. applying a sample liquid of the living organism to the functional surfaces of the at least two functional elements;
d. enriching sample material, preferably cells, DNA, RNA, proteins, peptides, synthetic molecules, at the detection receptors; and
e. withdrawing the detection device from the living organism.

14. The method of claim 13, in which the sample is enriched from: a blood vessel, efferent glandular ducts of the pancreas, of lacrimal glands, parotid glands, from efferent glandular ducts of mucous glands, mixed glands, cutaneous and sebaceous glands, mammary glands, spinal canals, cerebral ventricle systems, peridural spaces, gall bladders and their efferent anatomic structures, efferent urinary tracts or lymphatic systems, body cavities of the abdomen, the rib cage, the uterus, the urogenital apparatus, a joint or the gastrointestinal tract.

* * * * *